United States Patent [19]

Higashi et al.

[11] Patent Number: 4,750,940
[45] Date of Patent: Jun. 14, 1988

[54] NOVEL RESIN-COATED METALLIC PIGMENT AND A PROCESS FOR PRODUCING THE SAME

[75] Inventors: Katuyuki Higashi, Fuji; Yasunobu Imasato; Kiyoshi Iri, both of Ibaraki, all of Japan

[73] Assignee: Asahi Kasei Metals Limited, Tokyo, Japan

[21] Appl. No.: 902,604

[22] Filed: Sep. 2, 1986

[30] Foreign Application Priority Data

Sep. 7, 1985 [JP] Japan ................................ 60-198387
Jan. 9, 1986 [JP] Japan .................................... 61-1329

[51] Int. Cl.$^4$ ................................................ C09C 1/62
[52] U.S. Cl. ................................ 106/290; 106/308 M; 106/309
[58] Field of Search .................... 106/290, 308 M, 309

[56] References Cited

U.S. PATENT DOCUMENTS

| | | | |
|---|---|---|---|
| 3,519,593 | 7/1970 | Bolger | 106/308 Q |
| 3,884,871 | 5/1975 | Herman et al. | 260/42.14 |
| 3,941,731 | 3/1976 | Camelon et al. | 427/195 |
| 4,023,981 | 5/1977 | Perronin et al. | 106/308 N |
| 4,048,136 | 9/1977 | Kobayashi et al. | 524/440 |
| 4,205,997 | 6/1980 | Hesse et al. | 106/308 M |
| 4,395,485 | 7/1983 | Kashiwagi et al. | 106/308 M |
| 4,434,009 | 2/1984 | Banba | 106/308 M |

FOREIGN PATENT DOCUMENTS 0161470 12/1981 Japan .

Primary Examiner—A. Lionel Clingman
Assistant Examiner—Willie J. Thompson
Attorney, Agent, or Firm—Finnegan, Henderson, Farabow, Garrett & Dunner

[57] ABSTRACT

A resin-coated metallic pigment which comprises metal particles coated with a resin produced from (i) an ethylenically double-bonded unsaturated carboxylic acid and/or (ii) a phosphoric mono or diester having an ethylenical double bond and (iii) a monomer having at least three ethylenical double bonds and exhibits an alkali resistance index of up to 1.0 when subjected to an appropriate test, and a process thereof.

5 Claims, No Drawings

NOVEL RESIN-COATED METALLIC PIGMENT AND A PROCESS FOR PRODUCING THE SAME

FIELD OF THE INVENTION

The present invention relates to a novel resincoated metallic pigment and more particularly to a resincoated metallic pigment which, when used for paints, provides metallic coatings superior in chemical resistance, water resistance, cosmetic resistance, fingerprint resistance, etc., and when incorporated into a plastic by kneading, offers a compound having unprecedentedly high heat stability and storage stability.

DESCRIPTION OF THE PRIOR ART

Metallic pigments have been used for metallic paints, printing inks, plastic compounds, etc. to achive such decorating effect as to provide articles with metallic appearance which is regarded important to the articles. However, when used for metallic paints, the conventional metallic pigments during storage of the paints may react with their component resins, causing the paints to gel and become unfit for use. Another drawback of the conventional metallic pigments is that moisture contained therein may react with component metals, evolving gas and deforming the containers. The evalution of gas is markedly promoted by acid or alkali when it is present. Thus problems remain in the storage stability of paints containing metallic pigments.

Moreover, coatings from conventional metallic paints are unsatisfactory in chemical resistance including acid resistance and alkali resistance and in water resistance, and on standing, become discolored or deteriorated in gloss. Such instability limits the use of metallic paints.

Nevertheless, metallic coatings in recent years become used over a wide variety of applications. This is accompanied by growing needs for metallic coatings which have not only more enhanced chemical resistance and water resistance but also superior cosmetic resistance and fingerprint resistance. The cosmetic resistance means the power of inhibiting the phenomenon of leaving stains on coatings which is caused by cosmetic adhesion to the coatings. The fingerprint resistance is the power of inhibiting the phenomenon of developing black marks on coatings which results from finger touch on the substrates before coating. These phenomena both detract from the commercial value of metallic coatings to large extents.

When used for compounding with plastics, e.g. polyethylene and poly(vinyl chloride) resins, conventional metallic pigments, because of their deficiency in compatibility with resins, are not so uniformly dispersed as to yield intended homogeneous sheets or films. Moreover, when these pigments are blended with poly(vinyl chloride), their particle surfaces are discolored by hydrogen chloride generated from the poly(vinyl chloride) and the gloss of metallic pigments is lost.

For solving these problems, there have been proposed methods of coating metallic pigment particles with resins.

One of the known resin coating methods is to mix a pigment suspension in a liquid with a previously prepared resin solution in a solvent, thereby depositing the resin around the pigment particles (Japanese Patent Publication No. 3069/81).

According to this method, however, it is difficult to cause the resin to adhere uniformly and strongly to the surface of fine pigment particles. The resin coatings formed by this method adhere merely physically to the metal surface and hence the adhesive strength is weak. These resin coatings are peeled off or dissolved by external mechanical forces exerted in the pigment dispersion step of pigment production or by the dissolving or softening action of solvents which are contained in the paints produced from the resin-coated pigments. Thus, intended effects of resin coating are markedly impaired. In addition, the coating resin is liable to melt or soften on heating and hence does not have sufficient effect on pigments which will be used in plastic compounds.

Another method has been attempted, which comprises polymerizing a monomer in a dispersion of metallic pigment, thereby carrying out simultaneously resin production and pigment coating with the resin. For the purpose of establishing this method, it has been tried to form chemical bonds between a resin and the surface of metallic pigment particles (Japanese Patent Application Laid-Open No. 26837/75). However, this method has not yet been practiced commercially because of its production problems such that the process is complicated and the course thereof is long and additionally because of the insufficient improving effect of resin coating on the water resistance and chemical resistance since the formation of resin layers around pigment particles is not controlled.

Further there has been proposed a method of carrying out a polymerization in an aqueous dispersion of a metallic pigment under such conditions that the produced polymer will have electric charge under polymerization (Japanese Patent Publication No. 4029/78). However, this method also produces no sufficient effect of improving the water resistance, alkali resistance, and acid resistance and hence has not been put into industrial operation.

There are also known methods comprising coating pigment particles with a resin prepared by causing a polymerization to proceed in an organic solvent in which the monomer is soluble while the polymer is insoluble (Japanese Patent Application Laid-Open Nos. 161470/81 and 11818/76). However, also none of the resin-coated metallic pigments produced according to these inventions arrive yet at satisfactory levels for practical use in respect to chemical resistance, water resistance, and particularly cosmetic resistance and fingerprint resistance, thus requiring to be further improved. Moerover, when each resin-coated metallic pigment is mixed with a plastics by kneading and exposed to a high temperature (at least 150° C.), the resin covering the pigment is liable to soften and pigment particles may combine with one another. Thus the heat stability of these resin-coated pigments is insufficient to obtain intended films or sheets in which pigments are uniformly dispersed.

SUMMARY OF THE INVENTION

The present inventors made intensive studies to solve such problems of conventional metallic pigments as stated above. As a result, they found that the problems can be solved by coating metallic pigment particles with a resin of high-degree three-dimensional structure intimately and strongly attached to the surface of pigment particles by making the most of characteristics of a monomer having an ethylenical double bond and a carboxyl group in the molecule or characteristics of a phosphoric mono or diester having an ethylenical double bond in the molecule. Based on this finding, the present invention has been accomplished.

Accordingly, it is an object of the invention to provide a resin-coated metallic pigment which, on using for paints, will give metallic coatings superior in necessary properties such as chemical resistance and water resistance.

It is another object of the invention to provide a resin-coated metallic pigment for mixing with plastics which has unprecedentedly superior heat resistance and storage stability.

According to an embodiment of the invention, there is provided a resin-coated metallic pigment which comprises metal particles coated with a resin produced from (i) an ethylenically double-bonded unsaturated aliphatic carboxylic acid and/or (ii) a phosphoric aliphatic mono or diester having an ethylenical double bond and (iii) an aliphatic monomer having at least three ethylenical double bonds and exhibits an alkali resistance index of up to 1.0 when subjected to a prescribed test which will be described later, and said pigment undergoing no substantial agglomeration under prescribed heating test conditions which also will be described later.

According to another embodiment of the invention, there is provided a process for producing a resin-coated metallic pigment, which comprises the steps of;

dispersing a metallic pigment in an organic solvent and adding an ethylenically double-bonded unsaturated carboxylic acid and/or a phosphoric mono or diester having an ethylenical double bond and adding a monomer having at least three ethylenical double bonds and an initiator to polymerize said monomers.

The resin-coated metallic pigment according to the invention exhibits unprecedentedly high heat stability and such superior storage stability that, when the pigment it stored for a long perioed of time, agglomeration of the pigment is not observed and no change occurs in other properties (alkali resistance, water resistance, etc.) thereof which are given by the resin coating. In addition, when the present metallic pigment is used for metallic paints, the paints are superior in storage stability and will provide coatings which exhibit outstanding chemical resistance, water resistance, cosmetic resistance, and fingerprint resistance.

DETAILED DESCRIPTION OF THE INVENTION

Suitable ethylenically double-bonded unsaturated carboxylic acids (hereinafter simply referred to as carboxylic acid monomers) for use in the invention include acrylic acid, methacrylic acid, itaconic acid, and fumaric acid, which may be used alone or in combination. The amount of the carboxylic acid monomer used depends upon the kind, properties, and particularly the surface area of metallic pigment used. In general, the amount is between 0.01 and 10 parts by weight for 100 parts by weight of the component metal. When the amount is less than 0.01 part by weight, effects of the invention, that is to say, those on the water resistance, acid resistance, other chemical resistance, fingerprint resistance, etc. of the pigment, will be exhibited unsatisfactorily and during the next step of polymerizing the monomer having at least three ethylenical double bonds, the polymerization mixture will form a gel, which may make stirring infeasible. When the amount exceeds 10 parts by weight, the water resistance will lower. This may be attributable to excessive amounts of carboxyl groups contained in the resulting resin coating.

Suitable phosphoric esters having ethylenical double bonds (hereinafter these esters are simply referred to as phosphate monomers) for use in the invention include 2-methacryloyloxyethyl phosphate, di-2-methacryloyloxyethyl phosphate, tri-2-methacryloloxyethyl phosphate, 2-acryloyloxyethyl phosphate, di-2-acryloyloxyethyl phosphate, tri-2-acryloyloxyethyl phosphate, diphenyl-2-methacryloyloxyethyl phosphate, diphenyl-2-acryloyloxyethyl phosphate, dibutyl-2-methacryloyloxyethyl phosphate, dibutyl-2-acryloyloxyethyl phosphate, dioctyl-2-methacryloyloxyethyl phosphate, dioctyl-2-acryloyloxyethyl phosphate, 2-methacryloyloxypropyl phosphate, bis(2-chloroethyl) vinyl phosphonate, and diallyldibutyl phosphonosuccinate. These phosphate monomers also may be used alone or in combination.

Of these phosphate monomers, referred are monoesters. This is conceivably because phosphoric monoesters have two OH groups in the molecule and hence will be fastened more firmly to the surface of metallic such as aluminum pigment particles.

Particularly preferred phosphoric monoesters have a methacryloyloxy or acryloyloxy group in the molecule, including, for example, 2-methacryloyloxyethyl phosphate and 2-acryloyloxyethyl phosphate. Many of these monoesters are insoluble in common solvents for polymerization purposes.

The amount of the phosphate monomer used depends upon the kind, properties, and specially the surface area of metallic powder used. In general, the amount is between 0.01 and 30 parts by weight for 100 parts by weight of the component metal. When the amount is less than 0.01 part by weight, effects of the invention, that is to say, those on the water resistance, acid resistance, other chemical resistance, fingerprint resistance, etc. of the resulting coatings, will be exhibited unsatisfactorily. When the amount exceeds 30 parts by weight, said effects will scarcely increase.

Suitable monomers having at least three ethylenical double bonds in the molecule (hereinafter these monomers are simply referred to as crosslinking monomers) for use in the invention include, for example, trimethylolpropane triacrylate, trimethylolpropane trimethacrylate, tetramethylolmethane triacrylate, and tetramethylolmethane tetracrylate. These crosslinking monomers also may be used alone or in combination.

The crosslinking monomer is used in an amount of 2 to 50 parts by weight for 100 parts by weight of the component metal. When the amount is less than 2 parts by weight, effects of the invention such as the effect on the chemical resistance are limited, and when the amount exceeds 50 parts by weight, increase in the effects is no longer expected and the resulting metallic paint will be unfit for used since it gives coatings deteriorated in brilliance, gloss, and metallic appearance, which are fundamental properites of metallic coatings.

Another monomer having one or two polymerization reactive double bonds in the molecule may be used so far as it does not impair the effect of the invention, that is, such a monomer may be used in an amount of 0 to 10 parts by weight per 100 parts, by weight of the component metal. When the amount exceeds 10 parts by weight, the effect of the present invention is diminished, that is, the resulting resin-coated metallic pigment will provide coatings inferior in properties and will exhibit lowered heat stability, thus being unfit for practical use.

Suitable monomers having one or two polymerization-reactive double bonds in the molecule for use in the invention include styrene, α-methylstyrene, acrylic esters, e.g. methyl acrylate, methacrylic ester, e.g. methyl methacrylate, acrylonitrile, methacrylonitrile, vinyl acetate, vinyl propionate, ethylene glycol dimethacrylate, diethylene glycol dimethacrylate, triethylene glycol dimethacrylate, 1,3-butylene glycol dimethacrylate, neopentyl glycol diacrylate, and divinylbenzene. These monomers also may be used alone or in combination.

Polymerization initiators usable in the invention are compounds generally known as free-radical generators, including peroxides, e.g. benzoyl peroxide, lauroyl peroxide, isobutyl peroxide, and methyl ethyl ketone peroxide, and azobisisobutyronitrile.

The polymerization initiator is used in an amount of 0.1 to 50 parts, preferably 1 to 20 parts, by weight per 100 parts by weight of the crosslinking monomer. Less amounts of the initiator than 0.1 part by weight of said monomer are impractical since prolonged time is required for the polymerization. Exceeding 50 parts by weight, such amounts are also impractical because the polymerization proceeds so rapidly that it cannot be controlled.

The alkali resistance index used in the invention is the color difference ($\Delta E_H$) of a coating determined in accordance of JIS Z-8730 (1980) 6.3.2 from the colors of the coating measured in accordance with condition d(method 9-d) of JIS Z-8722 (1982) before and after immersion of the coating in a 0.1-N aqueous NaOH at 55° C. for 4 hours, said coating being prepared by applying a prescribed compounded paints.

The prescribed paint is a baking type of coating material composed of 100 parts by weight (nonvolatile content) of an acrylic-melamine mixed resin, 15 parts by weight of a pigment, and a necessary amount of a thinner. The acrylic resin used herein is a generally commercially available acrylic resin for baking use and the melamine resin is a generally commercially available butylated melamine resin. The mixing ratio of the acrylic resin to the melamine resin is from 70:30 to 90:10 by weight.

The resin-coated metallic pigment of the present invention gives an alkalic resistance index of up to 1.0, preferably up to 0.8. If the index exceeds 1.0, discoloration of the coating will be seen by visual observation, that is, the coating will not have sufficient alkali resistance. The pigment giving such coatings is not included in the scope of the invention.

A described hereinafter, the resin-coated metallic pigment which does not agglomerate substantially in a heat stability test undergoes practically no change in the particle size thereof when exposed to a prescribed temperature for a prescribed period of time. That is, the heat stability test is conducted in accordance with JIS K-5400 8.2.1 except that the test temperature is changed to 150° C., the heating time to 1 hour, and the amount of test specimen to 10 g. The degree of agglomeration is expressed by the ratio of $d'_2/d'_1$, wherein $d'_1$ and $d'_2$ are the respective particle sizes measured before and after heating of the specimen.

The resin-coated metallic pigment of the present invention has a $d'_2/d'_1$ ratio of up to 1.5, preferably up to 1.3. If the ratio exceeds 1.5, uniform dispersion of the metallic pigment will not be achievable in case of high-temperature processing thereof for compounding or molding.

The best process for producing the present resin-coated metallic pigment, i.e. a metallic pigment coated with a resin which is produced by polymerizing the carboxylic acid monomer and/or the phosphate monomer and the crosslinking monomer, comprises the first step of dispersing a metallic pigment in an organic solvent and adding the carboxylic acid monomer and/or the phosphate monomer and the second step of adding the crosslinking monomer and an initiator to polymerize said monomers.

In the first step, particles of the metallic pigment are dispersed in the organic solvent with stirring and keeping stirring, the carboxylic acid monomer and/or the phosphate monomer is added and stirring is further continued. These operations may be conducted at normal temperature or preferably under heating at a temperature of 30° to 80° C. for generally at least 5 minutes, preferably 10 minutes or more, though the first step may be regarded to be completed at the time when the concentration of the carboxylic acid monomer or the phosphate monomer becomes constant.

In the first step, a part or all of the crosslinking monomer can be added though this monomer is normally added in the second step.

It is preferable not to add this monomer in the first step, for the purpose of completing the first step rapidly and securely and for the purpose of preventing this monomer completely from polymerization initiation.

If the initiator for use in the second step is added in the first step, the resulting resin-coated metallic pigment will be inferior, of course, in performance characteristics, thus being scarcely fit for practical use.

It is assumed that, according to the above operations, carboxyl groups from the molecules of the carboxylic acid monomer and phosphate groups from the molecules of the phosphate monomer will be fixed to the surface of metallic pigment particles to yield pigment particles which have ethylenical double bonds on the surface.

This assumption is supported by the fact that, when the metallic pigment after completion of the first step is filtered off and the carboxylic acid monomer or the phosphate monomer remaining in the filtrate is determined, the result indicates a great decrease in the monomer quantity as compared with the initial quantity.

In the second step, the crosslinking monomer and the initiator are added with stirring to the dispersion prepared in the first step and the mixture is heated with stirring to allow the polymerization to proceed.

Thus, copolymerization occurs presumably by the reaction of double bonds of the carboxylic acid monomer and/or of the phosphate monomer which are previously fixed to the surface of metallic pigment particles, with the crosslinking monomer and thereby a highly crosslinked, densely reticulated resin layer is formed on the surface of each pigment particle. It is assumed that the effect of the present invention will be exhibited only by the formation of such resin layers having chemical bonds with surfaces of metallic pigment particles. This assumption is supported by the heat stability test result that the resin-coated metallic pigment of the invention exhibits much improved heat stability and practically no agglomeration.

The polymerization is desirably carried out in a reactor in which the air has been replaced with an inert gas such as nitrogen or argon. The reaction temperature is generally between 30° and 150° C. though dependent upon the kind of initiator used. The reaction period is between 30 minutes and 10 hours.

The crosslinking monomer and/or the initiator may be added either all at once or in parts.

When all the monomers and the initiator are added at once to initiate the polymerization immediately, the effect of the present invention is not exhibited.

When neither the carboxylic acid monomer nor the phosphate monomer is used and only the croslinking monomer is polymerized in the presence of metallic pigment particles dispersed in the organic solvent, that is, when the addition in the first step is omitted and the second step operation is directly started, not only the stirring of the polymerization mixture may become infeasible on account of a large increase in the viscosity of the mixture but also the resulting resin-coated metallic pigment will be much inferior in performance characteristics. This fact indicates that the surface of metal particles in this case is not sufficiently covered with the resin.

These data have proved that it is essential to perform the first step operation prior to the second step operation.

Suitable metals for the metallic pigment of the present invention include aluminum, copper, zinc, iron, nickel, and/or alloys of these metals, a preferred one of which is aluminum. The shape of the present metallic pigment may be flaky, spherical, acicular, or indefinite granular. Suitable particle sizes of the present metallic pigment depend upon the application purpose of the pigment. The average diameter of the particles may be in the range of about 1 to about 200 $\mu$ for paints and printing inks, and in the range of about 1 to about 100 $\mu$ for mixing with plastics. However, the present metallic pigment is not necessarily limited to these ranges.

A metallic pigment such as aluminum used as a starting material in the present invention is described below in detail. It is prepared by grinding fine pieces or granules of metallic pigment such as aluminum together with several % of a grinding aid by a mechanical means, for example, a stamp mill, dry type ball mill, wet type ball mill, attritor, or vibrating ball mill. This grinding aid affects physical properties of the resulting metallic pigment such as aluminum pigment as well as functions as a grinding aid. For this grinding aid there may be any of conventional ones including higher saturated or unsaturated acids, e.g. stearic acid and oleic acid and higher aliphatic amines, e.g. stearylamine. Regardless of the grinding aid used, the effect of the present invention can be obtained. Aluminum pigments produced by using stearic acid as a grinding aid are generally known as leafing type aluminum pastes and used in the form of silver paints to coat metal surfaces of tanks and the like for rust prevention. Aluminum pigments produced by using oleic acid or stearylamine are genrally known non-leafing type aluminum pastes and used in the form of metallic paints to coat automobiles, furniture, etc. for decoration purposes.

Suitable organic solvents for dispersing the metallic pigment in the first step include aliphatic hydrocarbons (e.g. hexane, heptane, octane, and mineral spirit), aromatic hydrocarbons (e.g. benzene, toluene, solvent naphtha, and xylene), esters (e.g. ethyl acetate, and butyl acetate) and ethers (e.g. tetrahydrofuran, diethyl ether). Such an organic solvent is used in an amount of 50 to 3000 parts by weight for 100 parts by weight of the component metal used, preferably 250 to 1000 parts by weight. When the amount is less than 50 parts by weight for 100 parts by weight of the component metal, the reaction mixture becomes such pasty that undesirably long time will be required for uniform diffusion of all the monomers and the polymerization initiator. When the amount exceeds 3000 parts by weight, the polymerization period is undesirably prolonged.

After resin coating layers have been formed around metallic pigment particles in the above described manner, the organic solvent is removed by filtration to such an extent that the filter cake will contain 30 to 80% by weight of nonvolatile matter, and if necessary, some other solvent and/or additives are added to make up a paste containing the resin-coated metallic pigment of the present invention.

Metallic paints produced from the resin-coated metallic pigment of the invention are composed of (i) 100 parts by weight a paint-purpose resin, (ii) 0.1 to 100 parts by weight the pigment, and (iii) a diluent thinner (a suitable amount).

The paint-purpose resin may be any of those used in conventional metallic paints. Other resins also can be used which have been unaccepted in the conventional metallic paints because of having many functional groups which are liable to react with metals and cause gelation. Examples of the paint-purpose resins usable in the present invention are acrylic resin, alkyd resin, oil-free alkyd resin, vinyl chloride resin, urethane resin, melamine resin, unsaturated polyester resin, urea resin, cellulosic resin, and epoxy resin. These resins may be used alone or in combination.

The resin-coated metallic pigment of the present invention for paints is used in an amount of 0.1 to 100 parts, preferably 1 to 50 parts, by weight per 100 parts by weight of the paint-purpose resin. When the amount of the pigment is less than 0.1 part by weight, such metallic paints will give coatings deficient in the necessary metallic luster. When the amount exceeds 100 parts by weight, the paints of such excess pigment contents are worse in coating workability and moreover give inferior quality coatings, thus being unfit for use.

Suitable diluent thinners for use herein are common organic solvents, including aromatic hydrocarbons, e.g. toluene and xylene, aliphatic hydrocarbons, e.g. hexane, heptane, and octane, alcohols, e.g. ethanol and butanol, esters, e.g. ethyl acetate and butyl acetate, ketones, e.g. methylethyl ketone, chlorine compounds, e.g. trichloroethylene, and cellosolves, e.g. ethylene glycol monoethylether. Preferably, two or more of these solvents are used by mixture. Composition of the mixture is chosen in consideration of the ability to solve the paint-purpose resin used and the film forming property and coating workability of the intended paint.

Metallic paints according to the present invention may contain additives used generally in the paint industry, such as pigments of other kinds, dyes, wetting agents, dispersants, antiflooding agents, levelling agents, slip agents, antiskinning agents, gelation inhibitors, and defoaming agents.

Test and measurement methods used in the present invention are described below in detail. In the following examples, test results are based on the following methods.

<Amount of coating resin on 100 parts by weight of component aluminum>

A paste (10 g) containing a resin-coated metallic pigment such as aluminum pigment of the invention is dispersed in 100 ml of chloroform (reagent grade) and the soluble fraction is extracted therein. The residual resin-coated pigment is dried in vacuo at 80° C. for 1 hour to give a powder, 1.0 g of which is weighed out and added in limited amounts into 200 ml of 6-N HCl (reagent grade) to dissolve the metallic portion. The residual insoluble resin portion is filtered, dried in vacuo at 80° C. for 14 hours, and weighed. From the found weight, the amount of resin is calculated per 100 parts by weight of the component metal.

<Alkali resistance index>

Using a resin-coated metal pigment such as aluminum pigment, a metallic paint of the following composition is prepared to evaluate the alkali resistance.

| Paint composition: | Parts by wt. |
| --- | --- |
| Resin-coated pigment (as nonvolatile matter) | 7.5 |
| Acrylic/melamine mixed resin*1 | 100 |
| Mixed thinner*2 | 180 |

*1Mixture of 80 parts by wt. of Acryldick 47-712 (nonvolatile content: 50%) and 20 parts by wt. of Superbeckamine J-820 (nonvolatile content: 50%) (supplied by Nippon Reichhold Co., Ltd.)
*2Mixture of toluene (70 parts), ethyl acetate (20 parts), and butyl-cellosolve (10 parts)

Then, this paint is applied by air-spraying on an aluminum plate (70×150×1 mm; supplied by Nippon Test Panel Co., Ltd.) to a coating thickness of 20 μ. The coated plate is dried at 140° C. for 30 minutes to prepare a coating for testing alkali resistance. A poly(vinyl chloride)cylinder (inner diameter 34 mm, height 15 mm) is fixed onto this coating by means of metal fastener, and 5 ml of 0.1-N aqueous NaOH is poured into the cylinder and left standing at 55° C. for 4 hours. Thereafter, the cylinder is removed and the test coating is thoroughly washed with water and dried.

The colors of the coating before and after alkali exposure are measured in accordance with condition d (method 9-d) of JIS Z-8722 (1982) and the color difference ($\Delta E_H$) is determined in accordance with JIS Z-8730 (1980) 6.3.2 (testing instrument: SH-4-MCH, supplied by Suga Shikenki Co., Ltd.).

<Acid resistance index>

The procedure of testing alkali resistance is repeated except for changing 0.1-N aqueous NaOH to 0.1-N aqueous $H_2SO_4$.

<Agglomeration test for heat stability>

A paste (10 g) containing a resin-coated metallic pigment such as aluminum pigment is taken in a weighing bottle, which is heated in an oven dryer at 150° C. for 1 hour. The particle size characteristic number ($d'_2$) of this pigment is determined by wet-screening it using mineral spirit as a dispersion medium and analyzing the result of this screening on the basis of the RRS particle size diagram (Rosin-Rammler-Spering particle size diagram) of DIN 4190. The particle size characteristic number $d'_1$ of the pigment before heating is also determined in the above manner. Then the ratio of $d'_2/d'_1$ is calculated.

In the screening, JIS standard sieves are used for particle sizes of 44 μ and more, and micro-mesh sieves (supplied by Buckbee-mears Co.) for particle sizes of less than 44 μ.

<Cosmetic resistance>

Using a resin-coated metallic pigment such as aluminum pigment, a paint for coating plastics of the following composition is prepared.

| Paint composition: | Parts by weight |
| --- | --- |
| Paste containing resin-coated pigment (as nonvolatile matter) | 9 |
| Thinner*1 | 40 |
| Acrylic resin*2 | 100 |
| Nitrocellulose resin solution*3 | 50 |

The viscosity of this paint is adjusted with the same thinner (*1) to 13 sec (Ford Cup #4, 20° C.), an ABS plate is spray-coated with this paint (coating thickness 10 μ), and dried at normal temperature for 3 days to prepare a coating, which is tested for cosmetic resistance.

A cosmetic cream Atrix hand cream, supplied by Kao Soap Co., Ltd. is applied on a half of the coating to a thickness of about 1 mm. Then this coating is allowed to stand for 5 days in a thermo-hygrostat controlled at a temperature of 60° C. and 90% RH.

Then the coating is washed with water, wiped to remove water, and dried at room temperature. Then, the appearance of the cosmetic-treated portion of the coating is compared with that of the untreated portion by visual observation.

<Fingerprint resistance>

A coating is prepared in the same manner as in the cosmetic resistance test except that a finger tip is pressed on the ABS plate to mark a finger-print in advance.

The test coating is immersed all in warm water at 60° C. for 3 hours. Thereafter, the coating is washed with water, wiped to remove water, and dried at room temperature for 1 hour. Intensity of fingerprint mark appearance on the coating is judged by visual observation.

EXAMPLE 1

A 1000-ml three-necked flask was fed with 115 g of an aluminum paste (M-601, supplied by Asahi Chemical Industry Co., Ltd., metal content 65.2%, average particle size 11 μ, flaky shape) and 400 g of mineral spirit. While introducing nitrogen gas into the flask, the mixture was stirred and heated to 80° C. Then, 0.375 g of acrylic acid (reagent grade) was added and stirring was continued for 30 minutes at 80° C. Secondly, 7.5 g of trimethylolpropane trimethacrylate (reagent grade) and 0.75 g of azobisisobutyronitrile (reagent grade) were added and the monomers were polymerized at 80° C. for 5 hours. Thereafter, the mixture in slurry form was allowed to cool to ordinary temperature and filtered to give a paste containing a resin-coated aluminum pigment. The nonvolatile matter content (according to JIS K-5910) in the paste was 51.0 wt. %. The amount of coating resin was 11.4 parts by weight per 100 parts by weight of the aluminum metal. This means that probably at least 99% of the total charged amount of acrylic acid, trimethylolpropane trimethacrylate, and azobisisobutyronitrile would adhere to the surface of aluminum particles. Coatings formed from this paste showed an alkali resistance index ($\Delta E_H$) of 0.3 and an acid resistance index ($\Delta E_H$) of 0.3, that is, the coatings exposed separately to alkali and acid as in the test methods showed practically no discoloration and maintained good quality.

Another coating formed from this paste was immersed in warm water of 60° C. for 7 days. As the result, practically no discoloration of the coating was observed and good quality thereof was maintained.

Moreover, when stored at 50° C. for a month, the paint composition containing this paste retained good properties without undergoing gelation or any other unfavorable change.

The heat stability test of this paste indicated that the ratio of $(d'_2/d'_1)$ was 1.05, i.e. no substantial agglomeration of the pigment particles was observed, and the appearance of the particles was uniform.

EXAMPLE 2

A 1000-ml three-necked flask was fed with 118 g of an aluminum paste (MG-21, supplied by Asahi Chemical Industry Co., Ltd., metal content 72.0%, average particle size 24 μ, flaky shape) and 325 g of mineral spirit. While introducing nitrogen gas into the flask, the mixture was stirred and heated to 80° C. Then 0.255 g of acrylic acid (reagent grade) was added and stirring was continued for 30 minutes at 80° C. Secondly, 4.25 g of trimethylolpropane trimethacrylate (reagent grade) and 0.43 g of azobisisobutyronitrile (reagent grade) were added and the monomers were polymerized at 80° C. for 5 hours. Thereafter, the mixture in slurry form was allowed to cool to ordinary temperature and filtered to give a paste containing a resin-coated aluminum pigment. The non-volatile matter content (according to JIS K-5910) in this paste was 60.2%. The amount of coating resin was 5.7 parts by weight per 100 parts by weight of the aluminum metal. This means that probably at least 98% of the total charged amount of acrylic acid, trimethylolpropane trimethacrylate, and azobisisobutyronitrile would adhere to the surface of aluminum particles.

The obtained resin-coated aluminum pigment of the present invention exhibited an alkali resistance index $(\Delta E_H)$ of 0.2, an acid resistance index $(\Delta E_H)$ of 0.1, and a ratio $(d'_2/d'_1)$ of 1.05 when subjected to the agglomeration test for heat stability.

EXAMPLE 3

A 1000-ml three-necked flask was fed with 104 g of an aluminum paste (4/62, supplied by Asahi Chemical Industry Co., Ltd., metal content 67.3%, average particle size 9 μ, flaky shape) and 400 g of mineral spirit. While introducing introgen gas into the flask, the mixture was stirred and heated to 80° C. Then, 0.525 g of acrylic acid (reagent grade) was added and stirring was continued for 30 minutes at 80° C. Secondly, 10.5 g of trimethylolpropane trimethacrylate (reagent grade) and 0.525 g of azobisisobutyronitrile (reagent grade) were added and the monomers were polymerized at 80° C. for 6 hours. Thereafter, the mixture in slurry form was allowed to cool to ordinary temperature and filtered to give a paste containing a resin-coated aluminum pigment. The nonvolatile matter content (according to JIS K-5910) in this paste was 53.0%. The amount of resin coating was 16.4 parts by weight per 100 parts by weight of the aluminum metal. This means that probably at least 99% of the total charged amount of acrylic acid, trimethylolpropane trimethacrylate, and azobisisobutyronitrile would adhere to the surface of aluminum particles.

The obtained resin-coated aluminum pigment of the present invention exhibited an alkali resistance index $(\Delta E_H)$ of 0.6, an acid resistance index $(\Delta E_H)$ of 0.1, and a ratio $(d'_2/d'_1)$ of 1.10 when subjected to the agglomeration test for heat stability.

EXAMPLE 4

A 1000-ml three necked flask was fed with 115 g of the same aluminum paste M-601 as used in Example 1 and 400 g of mineral spirit. While introducing nitrogen gas into the flask, the mixture was stirred and heated to 65° C. Then 0.375 g of methacrylic acid (reagent grade) was added and stirring was continued for 60 minutes at 65° C. secondly, 7.5 g of trimethylolpropane triacrylate (reagent grade) and 0.75 g of azobisisobutyronitrile (reagent grade) were added and the monomers were polymerized at 65° C. for 7 hours. Thereafter, the mixture in slurry form was allowed to cool to ordinary temperature and filtered to give a paste containing a resin-coated aluminum pigment. The nonvolatile matter content (according to JIS K-5910) in this paste was 47.5%. The amount of coating resin was 11.2 parts by weight per 100 parts by weight of the aluminum metal. This means that probably at least 97.4% of the total charged amount of methacrylic acid, trimethylolpropane triacrylate, and azobisisobutyronitrile would adhere to the surface of aluminum particles.

The obtained resin-coated aluminum pigment of the present invention exhibited an alkali resistance index $(\Delta E_H)$ of 0.4, an acid resistance index $(\Delta E_H)$ of 0.5, and a ratio $(d'_2/d'_1)$ of 1.08 when subjected to the agglomeration test for heat stability.

EXAMPLES 5-7 AND COMPARATIVE EXAMPLES 1-2

Pastes of resin-coated aluminum pigments were prepared from the same aluminum paste MG-21 as used in Example 2 by carrying out polymerization using monomers and an initiator as shown in Table 1 under the same conditions as applied in Example 2.

In Comparative Example 1, only trimethylolpropane trimethacrylate was polymerized, where stirring of the reaction mixture slurry became difficult in one hour after initiation of the polymerization on account of a rise in the viscosity of the slurry. This is conceivable because the treatment with acrylic acid was omitted and hence trimethylolpropane trimethacrylate would scarcely adhere to the surface of aluminum particles and the polymerization would proceed in the organic solvent (mineral spirit).

As shown in Table 1, the paste pigments of Examples 5-7 exhibited excellent performance characteristics while the pigment of Comparative Example 1 gave coatings inferior in alkali resistance. It is assumed that this pigment would not be coated with the resin. The paste pigment of Comparative Example 2 also showed performance characteristics inferior to those of Examples 5-7. This is attributable to the use of the excessive amount of acrylic acid, i.e. the presence of an excessive amount of carboxyl groups.

TABLE 1

| Amount of feed aluminum pigment | Amount of | Kind and amount of carboxylic | Kind and amount of crosslinking | Kind and amount of monomer having one polymerization-reactive | Amount of initiator |
| --- | --- | --- | --- | --- | --- |

TABLE 1-continued

|  | on dry basis (parts by wt.) | mineral spirit (parts by wt.) | acid monomer (parts by wt.) | monomer (parts by wt.) | double bond in the molecule (parts by wt.) | (AIBN) (parts by wt.) |
|---|---|---|---|---|---|---|
| Example 5 | 118 | 325 | AA 0.425 | TMPTMA 7.5 | ST 1.0 | 0.85 |
| Example 6 | 118 | 325 | AA 0.085 | TMPTA 4.25 | None | 0.085 |
| Example 7 | 118 | 750 | MA 0.425 | TMPTMA 7.5 | None | 0.75 |
| Comparative Example 1 | 118 | 325 | None | TMPTMA 7.5 | None | 0.75 |
| Comparative Example 2 | 118 | 325 | AA 25.0 | TMPTA 4.25 | None | 0.43 |
| Untreated aluminum paste MG-21 |  |  |  |  |  |  |

|  | Amount of coating resin per 100 parts by wt. of aluminum metal (parts by wt.) | Content of nonvolatile matter (%) | Alkali resistance test results Coating state | Acid resistance test results Coating state | Degree of pigment particle agglomeration evaluated in heat stability test $d'_2/d'_1$ |
|---|---|---|---|---|---|
| Example 5 | 11.3 | 59.1 | Good $\Delta E_H = 0.1$ | Good $\Delta E_H = 0.1$ | 1.04 |
| Example 6 | 5.1 | 60.2 | Good $\Delta E_H = 0.3$ | Good $\Delta E_H = 0.1$ | 1.08 |
| Example 7 | 10.1 | 57.5 | Good $\Delta E_H = 0.2$ | Good $\Delta E_H = 0.1$ | 1.05 |
| Comparative Example 1 | Gelation occurred in 1 hour after initiation of polymerization, making stirring infeasible 9.7 | 60.5 | Markedly discolored $\Delta E_H = 3.7$ | Discolored $\Delta E_H = 0.8$ | 1.10 |
| Comparative Example 2 | 29.0 | 60.1 | Discolored $\Delta E_H = 1.8$ | Discolored $\Delta E_H = 1.0$ | 2.50 |
| Untreated aluminum paste MG-21 | None | 72.0 | Markedly discolored $\Delta E_H = 4.5$ | Discolored $\Delta E_H = 1.2$ | Large blocks formed, Measurement of $d'_2$ was impossible |

AA Acrylic acid
MA Methacrylic acid
TMPTMA Trimethylolpropane trimethacrylate
TMPTA Trimethylolpropane triacrylate
ST Styrene
AIBN Azobisisobutyronitrile

EXAMPLES 8–9 AND COMPARATIVE EXAMPLE 3

Pastes of resin-coated aluminum pigments were prepared from the same aluminum paste M-601 as used in Example 1 by carrying out polymerization using monomers and an initiator as shown in Table 2 under the same conditions as applied in Example 1.

In Comparative Example 3, the polymerization was initiated by adding trimethylolpropane trimethacrylate, acrylic acid, and the initiator at the same time. The viscosity of the reaction mixture slurry rose in one hour after initiation of the polymerization. This is conceivably because the monomers would adhere insufficiently to the surface of aluminum particles and the polymerization of the monomers would proceed in the organic solvent (mineral spirit).

As shown in Table 2, the paste pigments of Examples 8–9 exhibited excellent performance characteristics while the pigment of Comparative Example 3 gave coatings inferior in alkali resistance. This is conceivably because this pigment would not be coated with the resin.

TABLE 2

|  | Amount of feed aluminum pigment on dry basis (parts by wt.) | Solvent (parts by wt.) | Kind and amount of carboxylic acid monomer (parts by wt.) | Kind and amount of crosslinking monomer (parts by wt.) | Kind and amount of monomer having one polymerization-reactive double bond in the molecule (parts by wt.) | Amount of initiator (AIBN) (parts by wt.) |
|---|---|---|---|---|---|---|
| Example 8 | 115 | Toluene 400 | Acrylic acid 0.75 | TMPTMA 10.0 | None | 1.0 |
| Example 9 | 115 | Mineral spirit 400 | Acrylic acid 0.75 | TMPTMA 10.0 | None | 1.0 |
| Comparative Example 3 | 115 | Mineral spirit 400 | (Added at the same time) Acrylic acid 0.75 | TMPTMA 10.0 | None | 1.0 |
| Untreated aluminum paste M-601 |  |  |  |  |  |  |

|  | Amount of coating resin per 100 parts by wt. of aluminum metal (parts by wt.) | Content of nonvolatile matter (%) | Alkali resistance test results coating state | Acid resistance test results coating state | Degree of pigment particle agglomeration evaluated in heat stability test $d'_2/d'_1$ |
|---|---|---|---|---|---|
| Example 8 | 15.5 | 50.1 | Good $\Delta E_H = 0.4$ | Good $\Delta E_H = 0.4$ | 1.08 |

TABLE 2-continued

| | | | | | |
|---|---|---|---|---|---|
| Example 9 | 15.6 | 48.8 | Good $\Delta E_H = 0.2$ | Good $\Delta E_H = 0.2$ | 1.03 |
| Comparative Example 3 | Gelation occurred in 1 Hour after initiation of polymerization, making stirring infeasible 15.5 | 46.3 | Discolored $\Delta E_H = 2.0$ | Discolored $\Delta E_H = 0.9$ | 1.09 |
| Untreated aluminum paste M-601 | None | 65.2 | Markedly discolored $\Delta E_H = 5.9$ | Markedly discolored $\Delta E_H = 3.0$ | Large blocks formed. Measurement of $d'_2$ was impossible |

TMPTMA Trimethylolpropane trimethacrylate

EXAMPLE 10

A paste containing a resin-coated aluminum pigment was prepared according to the procedure of Example 1 but using 2-methacryloyloxyethyl phosphate in place of acrylic acid. The non-volatile matter content (according to JIS K-5910) in this paste was 54.0% by weight.

The amount of resin coating was 11.4 parts by weight per 100 parts by weight of the aluminum metal. This means that probably at least 99% of the total charged amount of 2-methacryloyloxyethyl phosphate, trimethylpropane trimethacrylate, and azobisisobutyronitrile would adhere to the surface of aluminum particles.

This resin-coated aluminum pigment gave coatings which exhibited an alkali resistance index ($\Delta E_H$) of 0.2 and an acid resistance index ($\Delta E_H$) of 0.1, that is, the coatings subjected to the alkali resistance and acid resistance tests showed practically no discoloration and maintained good quality.

Another coating formed from this paste was immersed in warm water of 60° C. for 7 days. As the result, practically no discoloration of the coating was observed and good quality thereof was maintained. When stored at 50° C. for a month, the paint composition containing this paste retained good properties without undergoing gelation or any other unfavorable change.

The agglomeration test of this paste indicated that the ratio of ($d'_2/d'_1$) was 1.03, i.e. no substantial agglomeration of pigment particles was observed, and the appearance of the particles was uniform.

EXAMPLE 11

A paste containing a resin-coated aluminum pigment was prepared according to the procedure of Example 2 but using 2-methacryloyloxyethyl phosphate in place of acrylic acid. The nonvolatile matter content (according to JIS K-5910) in this paste was 59.0% by weight.

The amount of resin coating was 5.8 parts by weight per 100 parts by weight of the aluminum metal. This means that probably at least 99% of the total charged amount of 2-methacryloyloxyethyl phosphate, trimethylolpropane trimethacrylate, and azobisisobutyronitrile would adhere to the surface of aluminum particles.

The obtained resin-coated aluminum pigment of the present invention exhibited an alkali resistance index ($\Delta E_H$) of 0.3, an acid resistance index ($\Delta E_H$) of 0.2, and a ratio ($d'_2/d'_1$) of 1.10 when subjected to the agglomeration test for heat stability.

EXAMPLE 12

A paste containing a resin-coated aluminum pigment was prepared according to the procedure of Example 1 but using 2-acryloyloxyethyl phosphate in place of acrylic acid. The non-volatile matter content (according to JIS K-5910) in the paste was 51.0% by weight.

The amount of resin coating was 11.4 parts by weight per 100 parts by weight of the aluminum metal. This means that probably at least 99% of the total charged amount of 2-acryloyloxyethyl phosphate, trimethylolpropane trimethacrylate, and azobisisobutyronitrile would adhere to the surface of aluminum particles.

The obtained resin-coated aluminum pigment of the present invention exhibited an alkali resistance index ($\Delta E_H$) of 0.5, an acid resistance index ($\Delta E_H$) of 0.3, and a ratio ($d'_2/d'_1$) of 1.05 when subjected to the agglomeration test for heat stability.

EXAMPLE 13

A paste containing a resin-coated aluminum pigment was prepared according to the procedure of Example 2 but using 2.55 g of 2-methacryloyloxyethyl phosphate in place of 0.255 g of acrylic acid and changing the amount of trimethylolpropane trimethacrylate from 4.25 g to 8.5 g. The nonvolatile matter content (according to JIS K-5910) in this paste was 57.9% by weight.

The amount of resin coating was 13.4 parts by weight per 100 part by weight of the aluminum metal. This means that probably at least 99% of the total charged amount of 2-methacryloyloxyethyl phosphate, trimethyloylpropane trimethacrylate, and azobisisobutyronitrile would adhere to the surface of aluminum particles.

The obtained resin-coated aluminum pigment of the present invention exhibited an alkali resistance index ($\Delta E_H$) of 0.1, an acid resistance index ($\Delta E_H$) of 0.1, and a ratio ($d'_2/d'_1$) of 1.15 when subjected to the agglomeration test for heat stability.

COMPARATIVE TEST 1

(1) Preparation of resin-coated aluminum pigment of Comparative Example 4

A paste containing a resin-coated aluminum pigment was prepared according to the procedure of Example 1 using ethylene glycol dimethacrylate (reagent grade) in place of trimethylolpropane trimethacrylate. The nonvolatile matter content in this paste was 51.5% by weight.

(2) Preparation of resin-coated aluminum pigment of Comparative Example 5

A paste containing a resin-coated aluminum pigment was prepared according to the procedure of Example 10 but using ethylene glycol dimethyacrylate (reagent grade) in place of trimethylolpropane trimethacrylate. The nonvolatile matter content in this paste was 49.5% by weight.

The resin-coated aluminum pigments of Examples 1 and 10 were compared with those of Comparative Examples 4 and 5 referring to performance characteristics (alkali resistance, acid resistance, fingerprint resistance, cosmetic resistance, and the ratio of ($d'_2/d'_1$), i.e. agglomeration tendency on heating. As shown in Table 3, the results have revealed that the pigments of Examples 1 and 10 are much superior in those characteristics to the pigments of Comparative Examples 4 and 5.

TABLE 3

| Resin-coated aluminum pigment | Amount of resin coating per 100 parts by weight of aluminum metal | Alkali resistance test result Coating state | Acid resistance test result Coating state | Tendency to agglomeration on heating ($d'_2/d'_1$) | Cosmetic resistance | Fingerprint resistance |
|---|---|---|---|---|---|---|
| Example 1 | 11.4 | Good $\Delta E_H = 0.3$ | Good $\Delta E_H = 0.3$ | 1.05 | Good | Not developed |
| Comparative Example 4 | 10.6 | Slightly discolored $\Delta E_H = 1.3$ | Slightly discolored $\Delta E_H = 0.9$ | Agglomeration occurred 1.67 | Slight discoloration was observed | Fingerprint mark appeared |
| Example 10 | 11.4 | Good $\Delta E_H = 0.2$ | Good $\Delta E_H = 0.1$ | 1.03 | Good | Not developed |
| Comparative Example 5 | 10.5 | Slightly discolored $\Delta E_H = 1.2$ | Slightly discolored $\Delta E_H = 0.7$ | Agglomeration occurred 2.01 | Slight discoloration was observed | Fingerprint mark appeared |

What is claimed is:

1. A resin-coated metallic pigment which comprises metal particles coated with a resin produced from (i) an ethylenically double-bonded unsaturated carboxylic acid and/or (ii) a phosphoric mono or diester having an ethylenical double bond and (iii) a monomer having at least three ethylenical double bonds and exhibits an alkali resistance index of up to 1.0 when subjected to an appropriate test.

2. The resin-coated metallic pigment of claim 1, which undergoes no substantial agglomeration under definite heat stability test conditions.

3. The resin-coated metallic pigment of claim 1, wherein the phosphoric ester is 2-methacryloyloxyethyl phosphate or 2-acryloyloxyethyl phosphate.

4. A process for producing a resin-coated metallic pigment, which comprises the first step of dispersing a metallic pigment in an organic solvent and adding an ethylenically double-bonded unsaturated carboxylic acid and/or a phosphoric mono or diester having an ethylenical double bond and the second step of adding a monomer having at least three ethylenical double bonds and an initiator to polymerize said monomers.

5. The resin-coated metallic pigment of claim 2, wherein the monomer is a compound selected from the group consisting of trimethylolpropane triacrylate, trimethylolpropane trimethacrylate, tetramethylolmethane triacrylate, and tetramethylolmethane tetracrylate.

* * * * *